(12) United States Patent
Faber et al.

(10) Patent No.: US 7,593,766 B2
(45) Date of Patent: Sep. 22, 2009

(54) DETECTOR FOR ATRIAL FLUTTER AND ATRIAL FIBRILLATION

(75) Inventors: Thomas S. Faber, Freiburg (DE); Michael Lippert, Ansbach (DE); Marc Oliver Schweika-Kresimon, Herne (DE)

(73) Assignee: Biotronik CRM Patent AG, Baar (CH)

( * ) Notice: Subject to any disclaimer, the term of this patent is extended or adjusted under 35 U.S.C. 154(b) by 341 days.

(21) Appl. No.: 11/614,546

(22) Filed: Dec. 21, 2006

(65) Prior Publication Data

US 2007/0156058 A1  Jul. 5, 2007

Related U.S. Application Data

(63) Continuation-in-part of application No. 11/541,054, filed on Sep. 29, 2006, now Pat. No. 7,570,990.

(30) Foreign Application Priority Data

Sep. 30, 2005  (DE) ................... 10 2005 047 320

(51) Int. Cl.
*A61B 5/04* (2006.01)
(52) U.S. Cl. ................. 600/518; 600/509; 600/515; 607/14
(58) Field of Classification Search ................. 600/515, 600/518; 607/4–5, 7–8, 27–28
See application file for complete search history.

(56) References Cited

U.S. PATENT DOCUMENTS 4,291,699 A   9/1981  Geddes et al.
5,058,583 A  10/1991  Geddes et al.
5,267,599 A  12/1993  Kim (Continued)

FOREIGN PATENT DOCUMENTS

DE           19928659 A1   6/1999

(Continued)

OTHER PUBLICATIONS

German Search Report for priority application, dated Aug. 11, 2006.
European Search Report for priority application, dated Jun. 10, 2008.

*Primary Examiner*—Carl H Layno
*Assistant Examiner*—Jennifer Stewart
(74) *Attorney, Agent, or Firm*—Dalina Law Group, P.C.

(57) ABSTRACT

A detector for atrial fibrillation and/or atrial flutter comprises an atrial input for receiving an atrial signal representing an intraatrial electrogram or a time course of an intraatrial impedance, a ventricular input for receiving a ventricular event signal comprising information on an occurrence of a cyclically reoccurring ventricular event in chronological association to an atrial signal received via atrial input, an averaging unit adapted to average a plurality of sections of said atrial signal, each section to be considered for averaging starts or ends at a predetermined offset before a ventricular event, and to put out an averaged atrial signal, a peak amplitude determination unit adapted to determine peak-to-peak amplitude of said averaged atrial signal, and threshold comparator adapted to compare peak-to-peak amplitude of averaged atrial signal to predetermined reference value and to generate an AF warning signal if peak-to-peak amplitude of averaged atrial signal is less than predetermined threshold value.

23 Claims, 5 Drawing Sheets

U.S. PATENT DOCUMENTS

| | | |
|---|---|---|
| 5,433,729 A | 7/1995 | Adams et al. |
| 5,464,431 A | 11/1995 | Adams et al. |
| 5,464,432 A | 11/1995 | Infinger et al. |
| 5,486,199 A | 1/1996 | Kim et al. |
| 5,720,295 A | 2/1998 | Greenhut et al. |
| 2004/0010201 A1* | 1/2004 | Korzinov et al. ............ 600/518 |
| 2004/0078058 A1* | 4/2004 | Holmstrom et al. ........... 607/17 |
| 2004/0249420 A1* | 12/2004 | Olson et al. .................... 607/9 |
| 2005/0080347 A1* | 4/2005 | Sheth et al. ................. 600/515 |
| 2005/0159667 A1* | 7/2005 | Korzinov .................... 600/516 |
| 2006/0142811 A1* | 6/2006 | Militello ........................ 607/9 |
| 2007/0055170 A1* | 3/2007 | Lippert et al. ............... 600/547 |

FOREIGN PATENT DOCUMENTS

| | | |
|---|---|---|
| DE | 10361143 A1 | 12/2003 |
| DE | 102004034337 | 11/2005 |
| DE | 102004034337 A1 | 11/2005 |
| EP | 0583499 A1 | 8/1992 |
| EP | 1384433 | 1/2004 |
| WO | WO 2004/028629 | 4/2004 |

* cited by examiner

DETECTOR FOR ATRIAL FLUTTER AND ATRIAL FIBRILLATION

This application is a continuation in part of U.S. patent application Ser. No. 11/541,054, now U.S. Pat. No. 7,570,990 filed 29 Sep. 2006 which claims priority to German Patent Application DE 10 2005 047 320.2 filed Sep. 30, 2005 the specifications of which are both hereby incorporated herein by reference.

BACKGROUND OF THE INVENTION

1. Field of the Invention

The invention relates to a detector for atrial fibrillation and atrial flutter. Both types of atrial tachycardia are commonly referred to as AF herein after.

The invention also relates to an implantable medical device such as an implantable cardiac pacemaker or an implantable cardioverter/defibrillator (ICD) incorporating such detector and a method for detecting atrial fibrillation and atrial flutter.

2. Description of the Related Art

Atrial fibrillation is a cardiac state of disordered excitation of the atrial myocardium, possibly revolving around atrial flutter, in which the affected atrium is nearly unable to contribute its share to cardiac output. In an intraatrial electrocardiogram (intraatrial EGM) AF can be recognized by a high frequency atrial rate and a low amplitude.

Atrial fibrillation can be treated by means of implantable medical devices such as atrial defibrillators. Examples of atrial defibrillators and detectors for atrial fibrillation can be found in U.S. Pat. Nos. 5,267,559, 5,433,729, 5,464,431, 5,464,432, 5,486,199 and 5,720,295.

BRIEF SUMMARY OF THE INVENTION

In view of the prior art it is an object of the invention to provide an AF detector for reliable detection of AF that can be realized without excessive technical effort and that provides high sensitivity and high specificity.

According to this invention, the object is achieved by a detector that is adapted to process a plurality of atrial signals. Each atrial signal is representing the time course of an intraatrial impedance or an intraatrial electrogram within a time window that is synchronized with a ventricular event. The detector further is adapted to create an averaged atrial signal that is derived from the plurality of atrial signals. The detector is adapted to compare the maximum amplitude of the averaged atrial signal to a predetermined reference value. The detector is further adapted to generate an AF warning signal if the maximum amplitude of the averaged atrial signal does not exceed the predetermined threshold.

It should be noted, that the atrial signal can be either a section of the time course of an intraatrial impedance or a section of an intraatrial electrogram. The ventricular event that is used for synchronizing the time window for recording the time course of the atrial signal can be any ventricular event in the ventricular heart cycle. Since an R-wave is the most pronounced ventricular event, the ventricular event used for synchronizing the time window for recording the atrial signal preferably is an R-wave. The time window of the ventricular cycle begins with a predefined offset before the R-wave. The offset is preferable set to 300 ms to include the signal of the atrial contraction that precedes the corresponding ventricular contraction.

The invention is based on the recognition, that during periods of atrial flutter or atrial fibrillation, atrioventricular synchronization is lost. In other words, during periods of AF, excitation and contraction of the atrial myocardium usually is not in synchrony with ventricular excitation and contraction. Thus, peaks in the time course of the atrial signal do not occur at the same point of time with respect to the ventricular cycle, when the atrium exhibits flutter or fibrillation. Rather, the relative point of time of atrial excitation or contraction varies in relation to a ventricular contraction from ventricular heart cycle to ventricular heart cycle. If the average of the time course of the atrial signal is formed for a plurality of sections of the atrial signal over a number of ventricular heart cycles, the peaks of the time course of the atrial signal will almost disappear, since they occurred at different points of time with respect to the ventricular heart cycle.

According to a preferred embodiment, the AF detector comprises an impedance measurement unit with an input, to which an atrial electrode lead for unipolar or multipolar measurement of impedance in the atrium can be connected or is connected. The impedance measurement unit preferably is adapted to generate an unipolar or multipolar atrial impedance signal that comprises multiple impedance values of the atrial impedance at a plurality of time points for each atrial cycle. Preferably, the impedance measurement unit samples the intracardiac atrial impedance with a sampling rate that is higher, than the atrial rate during flutter or fibrillation.

The unipolar atrial impedance is measured between a neutral electrode having a relative large surface and an atrial electrode having a relatively small surface and being placed close to the wall of the atrium. The neutral electrode may be a housing of an implantable medical device such as an implantable atrial defibrillator. The atrial electrode may be a tip-electrode on an atrial stimulation lead.

Preferably, the impedance measurement unit is adapted to generate a pulsed current having constant peak amplitude. Said pulsed current preferably is delivered via the same electrodes that also serve for measuring a voltage drop resulting from the constant current pulses and due to the atrial impedance.

In an alternatively preferred embodiment, instead of such impedance measurement unit an atrial sensing unit that as such is known in the art is provided for picking up electrical potentials in the atrium that form an intraatrial electrogram. Preferably said intraatrial electrogram is sampled with a sampling frequency that is higher than an atrial rate of contractions during atrial flutter or fibrillation.

The AF-Detector further comprises an input for a ventricular signal that provides time points of ventricular events with respect to each time course of the atrial signals that shall be averaged. The ventricular signal may either be an intraventricular electrogram or it may be a signal that is derived from the ventricular electrogram such as signals of a ventricular marker channel. Preferably, the ventricular signal is a signal that reflects the instants of ventricular contractions in chronological assignment to the atrial signals to be averaged. For the invention it is not decisive, whether the ventricular signal is a raw signal, that is acquired by picking up electrical potentials in the ventricle or a signal that is derived from such raw signal such as marker signals from the ventricular marker channel.

The AF-detector further comprises an evaluation unit that is adapted to:
 average multiple sequential section of the atrial signal, each section representing the time course of the intraatrial impedance or the intraatrial electrogram starting and ending with a predefined time offset with respect to two consecutive ventricular events and
 to determine the maximum peak-to-peak amplitude of the averaged atrial signal and to compare the maximum peak-to-peak amplitude of the averaged atrial signal to a predetermined reference value, and to generate an AF warning signal in case that the a maximum peak-to-peak amplitude of the averaged atrial signal is less than the predetermined reference value.

The AF warning signals thus determined characterizes a cardiac state, wherein atrial flutter or atrial fibrillation is suspected.

With respect to averaging the atrial signal in synchrony with a ventricular event, it is preferred that the atrial signal is neither stretched nor compressed in the case of ventricular cycles of varying duration. Rather, either a first section or a final section of an atrial signal that extends beyond the duration of the shortest ventricular cycle is neglected or the extending section of atrial signals are averaged by dividing the sum of the remaining signals by the number of the contributing sections.

Turning now to FIG. 2 that is a schematic representation of some components of pacemaker 10 that are included in the metal housing 12 of pacemaker 10. It is to be noted that pacemaker 10 can comprise a number of further components not shown in FIG. 2 as it is readily appreciated by the man skilled in the art. In particular, if pacemaker 10 would be a full featured ICD, at least an atrial and a ventricular defibrillation shock generator would be provided.

The averaging of sections of the atrial signal over a predetermined number of immediately consecutive ventricular cycles has the effect, that peaks of the atrial signal will diminish if the atrial signal is not in synchrony to the ventricular signal whereas otherwise, if the atrial signal is in synchrony with the ventricular signal, peaks of the atrial signal are maintained if the atrial signal is averaged. Thus, a ventricle synchronized averaging of the atrial signal results in a characteristic reduction of the peak amplitude of the averaged atrial signal in case of atrial flutter or atrial fibrillation. This reduction of peak amplitude can be detected by comparing the peak-to-peak amplitude of the averaged atrial signal to a reference value. The peak-to-peak amplitude of the averaged atrial signal exceeds the reference value as long as the atrial signal is in synchrony with the ventricular signal whereas the peak-to-peak amplitude of the averaged atrial signal does not exceed the reference value in case of atrial flutter or atrial fibrillation.

Averaging of the sections of the atrial signal preferably is carried out in chronological association to an R-wave in the synchronous ventricular signal.

According to one embodiment, the atrial signal sections that are to be averaged, are sections of an intraatrial EGM. With respect to this embodiment, the atrial input of the detector is preferably connected to an atrial sensing stage that generates an intraatrial EGM-signal. Said intraatrial EGM-signal preferably is sampled with a sampling rate between 30 Hz and 300 Hz. Thus, the sampling rate is high enough to ensure that the sampled atrial signal comprises multiple signal values for each atrial cycle that includes an atrial contraction and an atrial relaxation immediately following said atrial contraction.

In an alternative embodiment, the detector comprises an impedance measuring unit. The impedance measuring unit comprises a measurement input that can be connected or that is connected to an atrial electrode lead for measurement of intraatrial impedance. The impedance measuring unit is adapted to generate an impedance signal that is used as the atrial signal to be averaged. The impedance signal comprises multiple impedance values for each atrial cycle or at least a section of an atrial cycle including an atrial contraction and an atrial relaxation immediately following said atrial contraction.

Preferably, the impedance measuring unit is adapted to sample the time course of the intraatrial impedance with a sampling rate between 30 Hz and 300 Hz.

With respect to impedance measurement, it is preferred that the impedance measuring unit is adapted to generate current pulses having amperage between 100 µA and 600 µA. The impedance measuring unit delivers said current pulses via a neutral electrode and an intraatrial electrode. The neutral electrode may be the housing of an implantable medical device. The impedance measuring unit is further adapted to measure a voltage drop between these two electrodes when delivering a current pulse.

Preferably, each current pulse has an identical duration between 10 µs and 20 µs. It is further preferred, that the impedance measuring unit generates pairs of current pulses wherein each pair is formed by two current pulses having the same magnitude and duration but alternating polarity. In order to avoid polarisation artefacts, it is further preferred that the impedance measuring unit generates a sequence of pairs of current pulses wherein the sequence of polarity of each current pulse alternates from pair to pair. E.g. the first pair of current pulses begins with current pulse having a positive polarity and ends with a current pulse having a negative polarity whereas the immediately following pair of current pulses begins with a current pulse having a negative polarity and ends with a current pulse having a positive polarity and so on.

In order to increase the specificity of the AF detector, it is preferred that the detector comprises a Wenckebach discriminator. The Wenckebach discriminator is adapted to respond to an AF warning signal and to discriminate AF from an AV block II° Wenckebach type. If an AV Block II° Wenckebach type is detected, the AF warning signal is cleared.

The preferred embodiment of the AF detector comprising a Wenckebach discriminator solves the problem, that the reduction of the peak amplitude of the averaged atrial signal may also occur in case of an AV block II° Wenckebach type even in absence of AF. This is because in case of AV block II° Wenckebach type synchronicity between atrial contractions and ventricular contractions may be lost.

In case of an AV block II° Wenckebach type fatigue of the natural atrioventricular conduction leads to an increase of the duration of PQ intervals up to a point where the atrioventricular conduction fails. The PQ interval is the duration between an atrial depolarisation and contraction and the beginning of the ventricular depolarisation and contraction. Depending on whether the increase in duration of PQ intervals remains constant from heart cycle to heart cycle or increases, the RR-intervals that represent the duration of a ventricular cycle can remain constant over a plurality of consecutive ventricular cycles or can increase until the atrioventricular conduction fails. As a consequence periodically multiple of ventricular cycles with nearly constant RR-intervals occur that are followed by a relatively long duration ventricular cycle exhibiting a relatively long RR-interval or, if a pacemaker in a dual chamber mode becomes active, a ventricular cycle exhibiting a relatively shorter cycle length.

The Wenckebach discriminator is provided to discriminate an AV block II° Wenckebach type from AF by means of stability criteria. In one preferred embodiment the Wenckebach discriminator determines an averaged ventricular cycle length over a predetermined number of N recent ventricular cycles. The averaged ventricular cycle length preferably is an averaged RR-interval RRm or even preferred the median of said predetermined number of RR-intervals. In case only a single ventricular cycle is detected that exhibits a duration outside a predetermined stability range, an AV block II° Wenckebach type is detected and no AF warning signal is put out. The predetermined stability range preferably is defined by a stability threshold that refers to the average ventricular cycle duration and that defines a maximum tolerated difference to said averaged duration of ventricular cycles. Thus, the stability range is defined by $$RRm \times (1+/-d)$$

with d being the stability threshold.

In case of an eventual occurrence of two consecutive RR-intervals outside said stability range, the Wenckebach discriminator does not detect a AV block II° Wenckebach type and confirms the AF warning signal.

In a particularly preferred embodiment, the Wenckebach discriminator is adapted to act as follows:

For the case that the peak amplitude of the averaged atrial signal has sunk below the reference value and thus an AF warning signal was generated, the Wenckebach discriminator is triggered to generate a counter value as disclosed further below. Alternatively, the Wenckebach discriminator may be permanently active or can be triggered by an AF warning signal. If the Wenckebach discriminator is active, it determines a present stability range by multiplying the averaged ventricular cycle length RRm for a number of N recent ventricular cycles with two factors that define the upper and the lower stability threshold of each present stability range. One factor is the sum of 1 plus a predetermined difference value d, with d being for example 0.25, and the other factor is the sum of 1 minus d, respectively. The averaged ventricular cycle duration of N ventricular cycles can be the mean value of current N RR-intervals or—in a preferred embodiment—the median of said number N of recent RR-intervals. Alternatively, the averaged ventricular cycle duration can be generated by a recursive filter wherein N forms a "time constant". A suitable value for the number N is between 5 and 8 for all cases mentioned above.

When active, the Wenckebach discriminator determines for each ventricular cycle whether the respective RR-interval is within the stability range RRm×(1+/−d) or not. If a current RR-interval is outside a present stability range and if a next RR-interval following the current RR-interval is again within the stability range, a counter value of a counter of the Wenckebach discriminator is incremented by one. Said counter value of the counter of the Wenckebach discriminator can be incremented up to a maximum counter value Nmax of e.g. 20, such that the counter value can not be further incremented if Nmax is reached. As soon as two consecutive ventricular cycles are having a cycle length that is outside the stability range or if a plurality of e. g. 20 consecutive RR-intervals exhibit a cycle length within the stability range, the counter value of the counter is decremented by one. If the counter value of the counter of the Wenckebach discriminator reaches a counter threshold Nth of e. g. 10, the Wenckebach discriminator detects an AV block II° Wenckebach type and clears the AF warning signal. Thus, it is avoided that for example an atrial defibrillation is triggered if an AV block II° Wenckebach type is present rather than an atrial fibrillation.

Instead of determining the stability of RR-intervals as disclosed herein before, the Wenckebach discriminator can be adapted to evaluate the stability of the ventricular rate of contractions.

The object of the invention is also solved by a method for detecting atrial flutter and/or atrial fibrillation, said method comprising the steps of:

acquiring an atrial signal over a time period that includes multiple ventricular heart cycles, acquiring a ventricular signal in chronological association with said atrial signal, determining a plurality of sequential sections of said atrial signal wherein each section begins or ends at a predefined time offset before the instant of a ventricular event derived from said ventricular signal, averaging said plurality of sections of the atrial signal thus forming an averaged atrial signal, determining the peak-to-peak amplitude of said averaged atrial signal, comparing said peak-to-peak amplitude to a predetermined reference value, and generating an AF warning signal if said peak-to-peak amplitude is less than said predetermined reference value.

Preferred embodiments of the method correspond to the preferred embodiments of the AF detector as pointed out above.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best not presently contemplated for caring out the invention. This description is not to be taken in a limiting sense, but is made nearly for the purpose of describing the general principles of the invention. The scope of the invention should be determined with reference to the claims.

Figure 1:
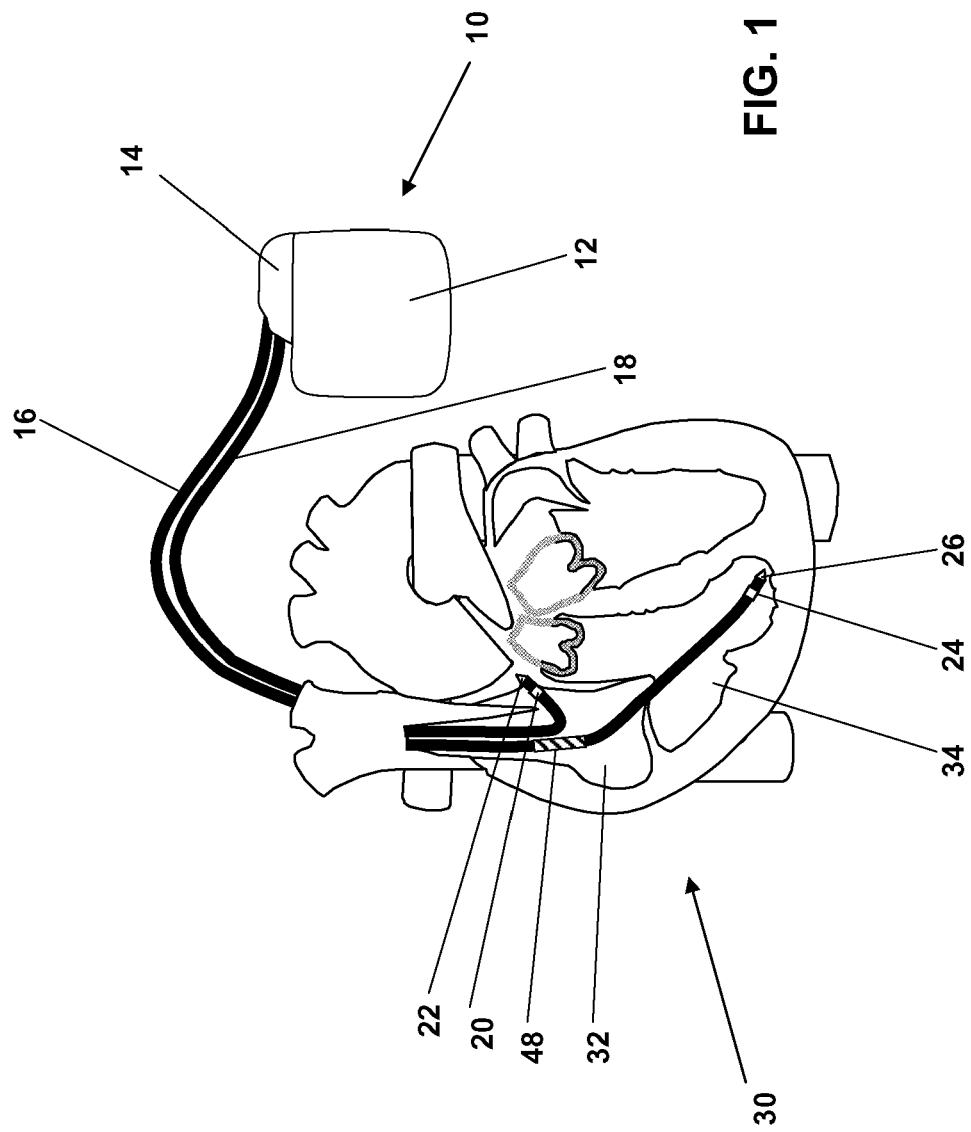
FIG. 1 shows a dual chamber pacemaker connected to leads placed in the heart.

In FIG. 1, a dual chamber pacemaker 10 is illustrated that is connected to a heart by means of pacing/sensing leads 16 and 18.

Pacemaker 10 comprises a hollow housing 12 made from a biocompatible metal such as titanium. Pacemaker 10 comprises a transparent header 14 that is made from electrically insulating plastic and that encloses terminals to which electrode leads 16 and 18 are connected detachably. Electrode leads 16 and 18 each comprise a proximal connector (not shown) that is plugged into the connectors of header 40.

Electrode lead 16 is an atrial electrode lead bearing an atrial tip electrode 22 at its distal end and an atrial ring electrode 20 close to its distal end.

Electrode lead 18 is a ventricular electrode lead bearing a ventricular tip electrode 26 at its distal end and a ventricular ring electrode 24 close to its distal end. Further, ventricular electrode lead 18 is bearing an atrial fibrillation electrode 48 that is placed proximal from ventricular ring electrode 24 in a distance suitable for the atrial defibrillation electrode 50 to be placed in the atrium 32 of a heart 30.

As it is apparent from FIG. 1, the distal end of atrial electrode lead 16 is placed in atrium 32 of the heart 30, when implanted. The atrial ring electrode 20 and the atrial tip electrode 22 are both placed in the right atrium 32 of the heart 30. Atrial tip electrode 22 touches the wall of atrium 32 and thus has direct contact to the atrial myocardium.

The distal end of ventricular electrode lead 18 is placed close to an apex of a right ventricle 34 of the heart 30. Both, the ventricular tip electrode 26 and the ventricular ring electrode 24 are placed in the right ventricle 34. The ventricular tip electrode 26 touches the wall of ventricle 34 close to its apex and thus has direct contact to the myocardium (the heart tissue) of the ventricle 34.

As already pointed out, a larger surface atrial defibrillation electrode 48 is provided on ventricular electrode lead 18 such that the atrial defibrillation electrode 48 is placed in the right atrium 32 of the heart 30, when said ventricular electrodes 24 and 26 are placed in close proximity to the apex of the right ventricle 34. By means of the atrial defibrillation electrode 48, pacemaker 10 not only can act as dual chamber pacemaker for stimulating the right ventricle 34 and the right atrium 32 but also can act as an atrial defibrillator. As it is understood by the man skilled in the art, also a ventricular defibrillation electrode can be provided on the ventricular electrode lead 18 to enable the pacemaker 10 to deliver ventricular defibrillation shocks to the right ventricle 34 if needed. Thus, pacemaker 10 can be a dual chamber implantable cardioverter/defibrillator (ICD).

Figure 2:
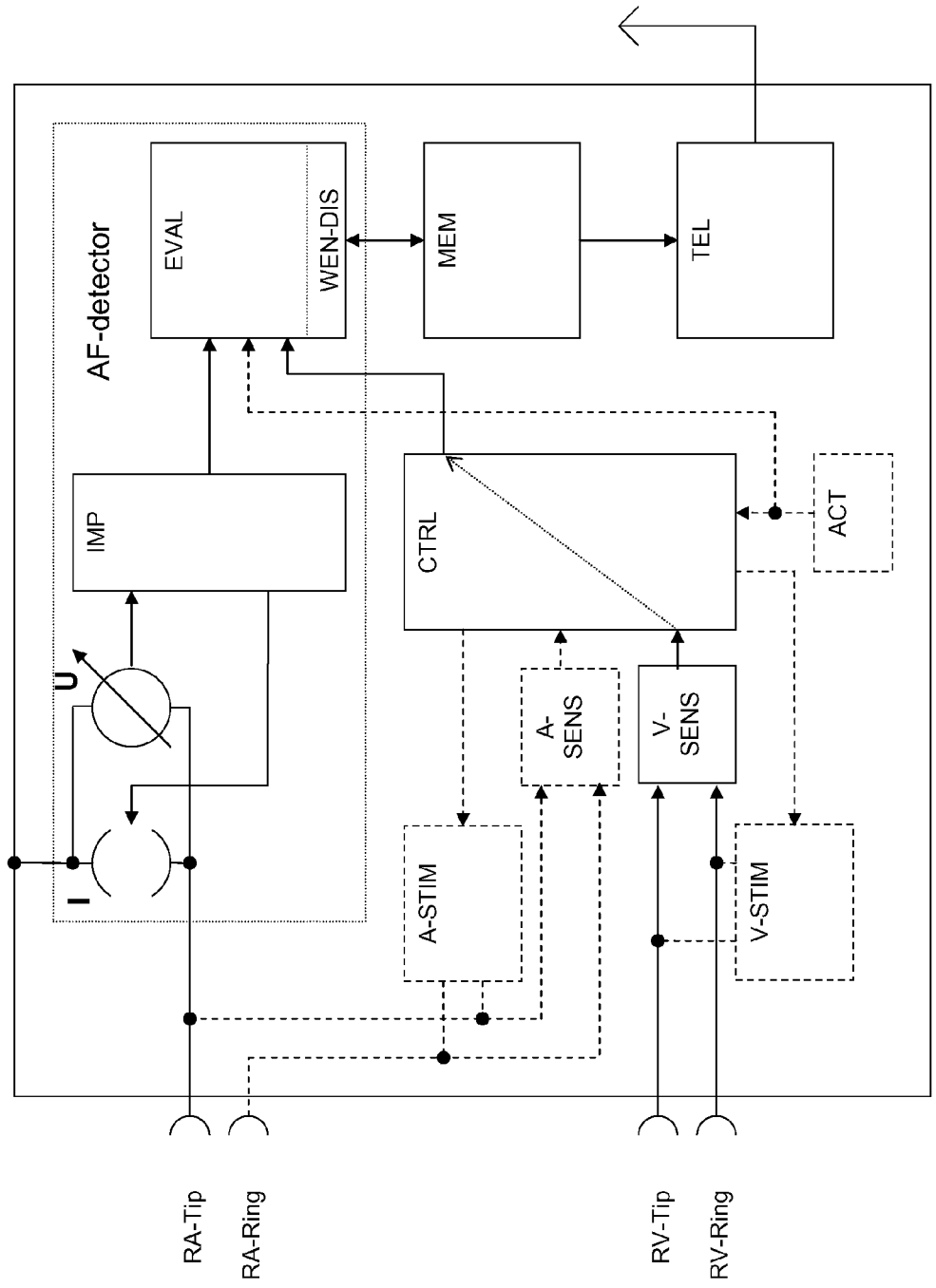
FIG. 2 is a block diagram of the pacemaker of FIG. 1 comprising the AF detector according to the invention.

The components enclosed in housing 12 are connected via header 14 with electrode leads 16 and 18. In FIG. 2 four terminals are schematically illustrated, a terminal RA ring for the right atrial ring electrode 20, a terminal RA tip for the right atrial ring electrode 22, a terminal RV ring for the right ventricular ring electrode 24 and a terminal RV tip for the right ventricular tip electrode 26. A terminal for the right atrial defibrillation electrode 48 is not shown in FIG. 2 although such terminal and an atrial defibrillation shock generator could also be present within housing 12 of pacemaker 10.

Terminals AR ring and AR tip are electrically connected to an atrial stimulation unit A-STIM and an atrial sensing unit A-SENS. Thus, electrical potentials picked up in the atrium can be fed to the atrial sensing unit A-SENS and electrical stimulation pulses can be delivered from the atrial stimulation pulse generator A-STIM via e.g. atrial tip electrode 22 to the myocardium of the right atrium. Terminals RV-ring and RV-tip are connected to a ventricular stimulation pulse generator V-STIM and a ventricular sensing unit V-SENS. Thus, electrical potentials picked up in the ventricle can be fed to the ventricular sensing unit V-SENS and ventricular stimulation pulses generated by ventricular stimulation pulse generator V-STIM can be delivered to the apex of the right ventricle 34 of the heart 30 via a right ventricular electrode lead 16.

The atrial stimulation pulse generator A-STIM and the atrial sensing unit A-SENS as well as right ventricular stimulation pulse generator V-STIM and the right ventricular sensing unit V-SENS are commonly connected to a control unit CTRL. Control unit CTRL receives the output signals from the atrial sensing unit A-SENS and from the ventricular sensing unit V-SENS. The output signals of sensing units A-SENS and V-SENS are generated each time that a P-wave representing an intrinsic atrial event or an R-wave representing an intrinsic ventricular event, respectively, is detected by evaluating the time course of an intraatrial EGM or an intraventricular EGM picked up in the right atrium 32 or the right ventricle 34, respectively. An As signal is generated, when the atrial sensing unit A-SENS detects a P-wave and a Vs signal is generated when the ventricular sensing unit V-SENS detects an R-wave.

Atrial and ventricular stimulation pulse generators A-STIM and V-STIM, respectively, are adapted to generate electrical stimulation pulses for pacing a respective heart chamber whenever triggered by control unit CTRL, according to programmed tuning regime.

Figure 3:
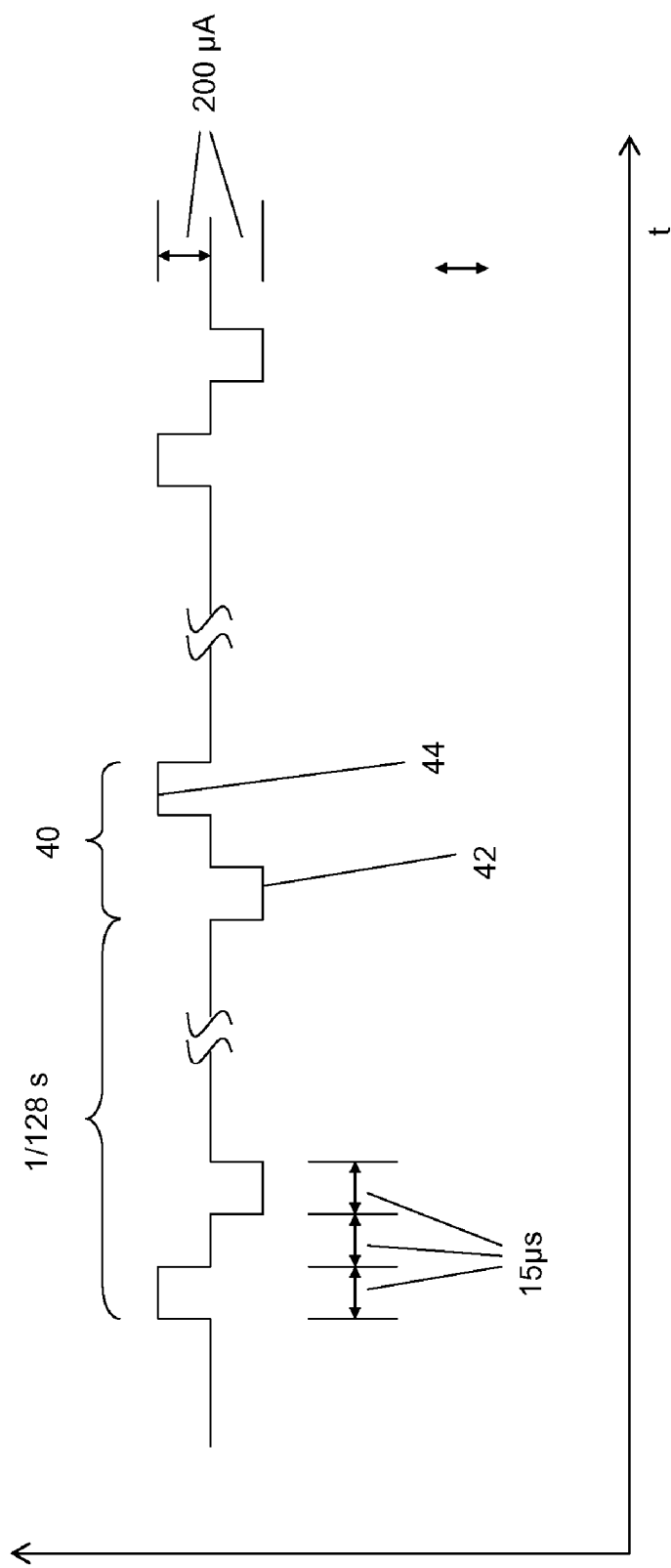
FIG. 3 is a representation of a current used for measuring the intraatrial impedance with the pacemaker of FIGS. 1 and 2.

With respect to one preferred embodiment of the present invention, it is to be noted, that terminal RA-tip is also connected to an impedance measuring unit that comprises a constant current source I, a voltage measuring unit U and an impedance signal generator IMP. The constant current source I and the voltage measurement unit U are also connected to the housing 12 of pacemaker 10 forming a neutral electrode. The impedance signal generator IMP of the impedance measuring unit is adapted to sample a voltage drop measured by voltage measurement unit U with a sampling rate between 30 Hz and 300 Hz, preferably 128 Hz. Constant current source I generates a sequence of pairs 40 of constant current pulses with a rate corresponding to the sampling rate. Each pair of constant current pulses comprises two consecutive current pulses 42 and 44 having the same magnitude and duration but different polarity. The sequence of polarities of the pairs 40 of current pulses alternates as it is depicted in FIG. 3.

A preferred sampling rate is 128 Hz. Each pair 40 of constant current pulses preferably has a total duration of 45 µs wherein each constant current pulse has a duration of 15 µs. The two current pulses making one pair of current pulses are spaced in time by 15 µs.

Figure 5:
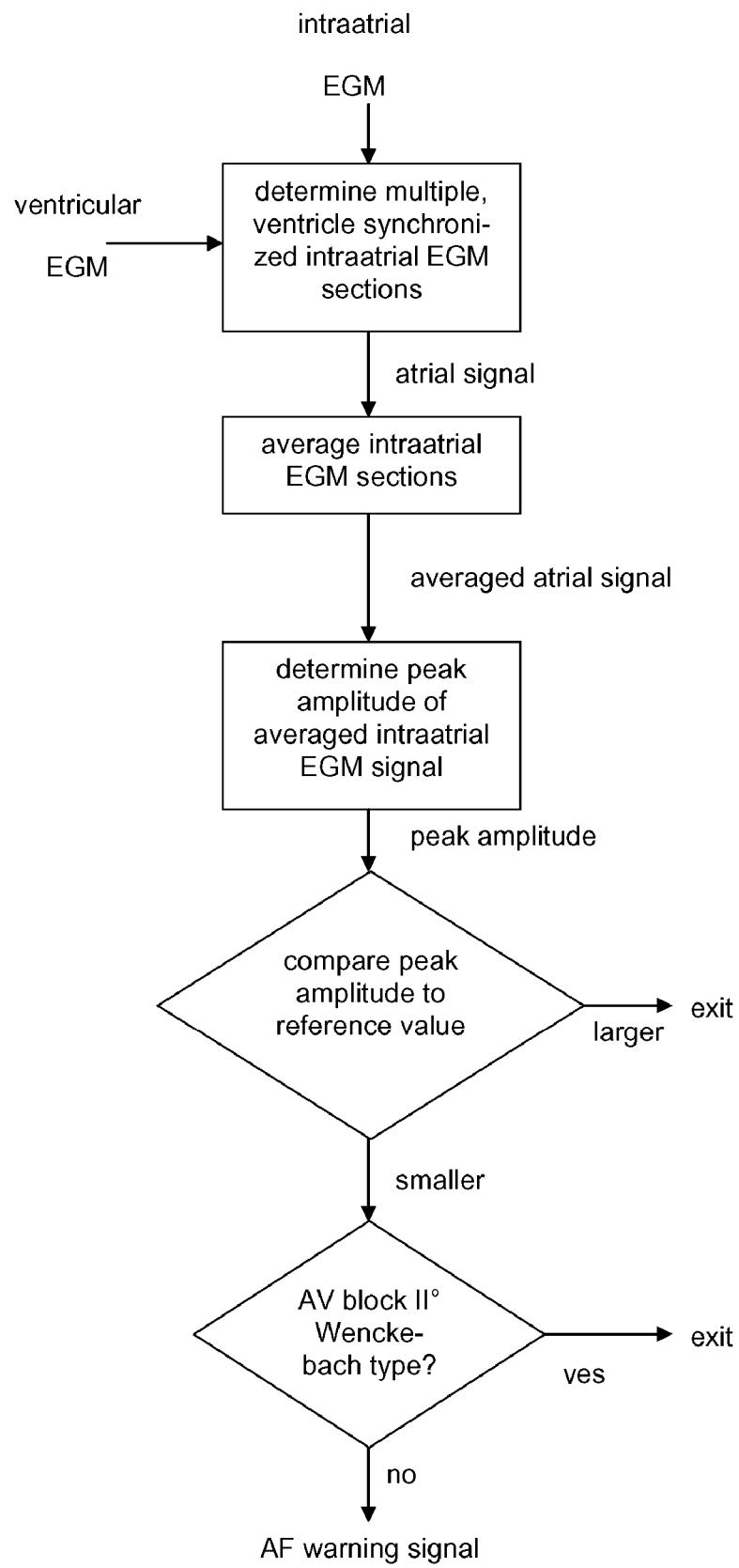
FIG. 5 is a flow chart illustrating a method for detection of AF according to the invention.

The atrial impedance signal thus derived is fed to an evaluation unit EVAL that is part of an AF detector that in turn is part of pacemaker 10. The evaluation unit EVAL comprises an atrial signal input that is connected to the impedance signal generator IMP and a ventricular signal input that is connected to control unit CTRL. Thus, the evaluation unit EVAL can receive an atrial signal from the impedance measuring unit wherein the atrial signal is a sampled atrial impedance signal. Furthermore, the evaluation unit EVAL can receive a ventricular signal from control unit CTRL that comprises information on the occurrence of ventricular events such as R-waves in chronological assignment to the atrial signal. FIG. 5 is a flow chart illustrating a method for detection of AF according to the invention. The evaluation unit EVAL is adapted to divide the atrial signal in sections which each begin or end at a predefined offset before the instant of a ventricular event. Thus, multiple sequential sections of the atrial signal are formed. Preferably, the detector is adapted to average a sequence of a total number of 8 latest sections of the atrial signal. Evaluation unit EVAL averages said plurality of sections of the atrial signal in order to generate an averaged atrial signal. Then, the evaluation unit EVAL determines the peak-to-peak amplitude of the averaged atrial signal and compares the peak-to-peak amplitude to a predetermined reference value. If the peak-to-peak amplitude of the averaged atrial signal exceeds the reference value, no AF warning signal is generated. Otherwise, if the peak-to-peak amplitude of the averaged atrial signal is less than the reference value, an AF warning signal is generated unless it is cleared by a Wenckebach discriminator that is described later on herein. The principles of generating an AF warning signal based on an averaged atrial signal are already mentioned at an earlier part of this description. Therefore, no further explanation is needed here.

It should be noted, that the impedance measuring unit comprising constant current source I, voltage measurement unit U and impedance signal generator IMP can be omitted in an alternative embodiment of the invention. Instead, an atrial EGM as generated by the atrial sensing unit A-SENS can be used as the atrial signal that is averaged and evaluated by evaluation unit EVAL.

The ventricular signal that is fed to the ventricular signal input evaluation unit EVAL is generated by means of the ventricular sensing unit V-SENS. The intraventricular electrogram generated by the ventricular sensing unit V-SENS can be directly fed to the ventricular signal input of evaluation unit EVAL. Alternatively, control unit CTRL may be adapted to derive marker signals from the intraventricular EGM received from the ventricular sensing unit V-SENS and to pass on ventricular marker signals chronologically corresponding to the instant of occurrence of R-waves to the ventricular signal input of evaluation unit EVAL.

As already mentioned earlier herein, the number of sections of the atrial signal to be averaged by the evaluation unit EVAL in synchrony with ventricular signals preferably is 8.

To further illustrate the concept, the invention is based on, a short notice to the behaviour of a healthy heart not exhibiting any atrial flutter or atrial fibrillation is given in the following. In a healthy heart, an atrial contraction is followed by a ventricular contraction after a relatively constant atrial ventricular conduction time, so that a synchronicity exists between atrial and ventricular contractions. The averaged atrial impedance signal for a healthy heart thus would reproduce a typical time course of the atrial impedance between two consecutive ventricular contractions and exhibit a peak amplitude at an instant when the atrial contraction usually takes places with respect to the ventricular cycle. The instant of the peak amplitude of the time course of the atrial impedance occurs prior to a next ventricular contraction that has a chronological spacing to the ventricular contraction, that nearly corresponds to the atrial ventricular conduction time.

As already described earlier herein, such synchronicity between atrial contractions and ventricular contractions is lost in a case of atrial flutter and atrial fibrillation and thus can be detected by a diminishing peak amplitude of the averaged atrial signal.

Since the loss of atrial ventricular synchrony can also be due to an AV block II° of Wenckebach type, in a preferred embodiment of the invention also a Wenckebach discriminator is provided. Such Wenckebach discriminator to WEN-DIS is part of the AF detector and the evaluation unit EVAL and can clear an AF warning signal under certain conditions that are illustrated hereinafter.

The present invention makes use of this state of affairs in that the analysis unit EVAL detects a nonexistent atrioventricular synchronicity by analyzing the averaged atrial impedance signal. For this purpose, the peak amplitude of the averaged atrial impedance signal is compared to a comparison value and a nonexistent atrioventricular synchronicity is detected when the peak amplitude of the atrial impedance signal is less than the comparison value. Since a nonexistent atrioventricular synchronicity may also have its origin in an AV block II° Wenckebach type, the analysis unit EVAL, in the preferred embodiment variation shown here, additionally has a Wenckebach discriminator in the way described at the beginning, if the analysis unit EVAL has first established a lack of atrioventricular synchronicity and subsequently generated an AV suspicion signal. The Wenckebach discriminator WEN-DIS acts as a type of filter in the output of the analysis unit EVAL and ensures that the analysis unit EVAL only outputs an AF suspicion signal if the analysis unit has established the lack of atrioventricular synchronicity and, in addition, the Wenckebach discriminator has established the non-existence of an AV block II° Wenckebach type.

Figure 4:
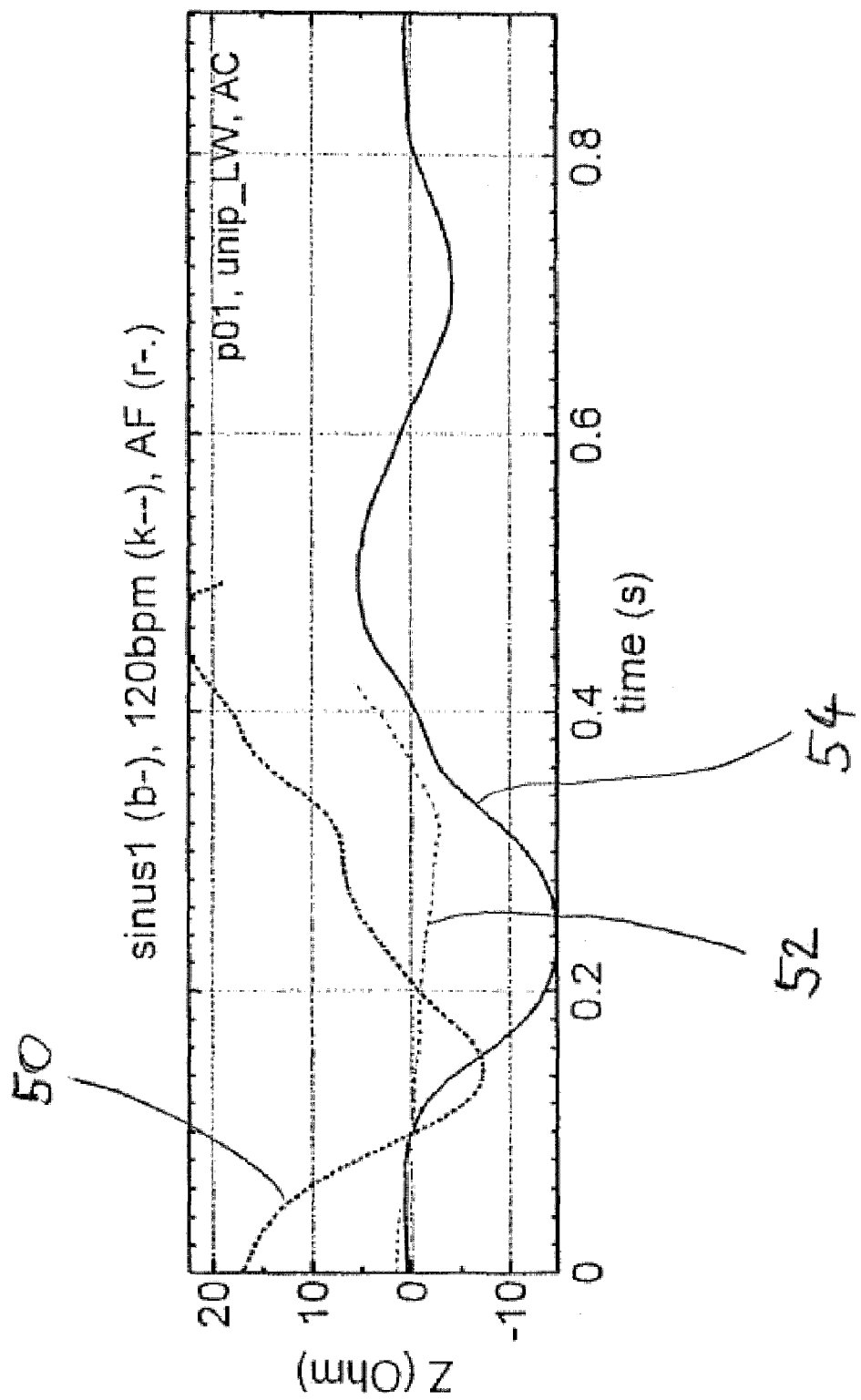
FIG. 4 shows examples of the change of peak amplitude of averaged intraatrial impedance signals for different states of heart.

Three different intraatrial impedance curves are shown in FIG. 4 to explain the mode of operation of the analysis unit EVAL, namely for the case of the healthy heart (curve 54), for the case of the stimulated heart (curve 50), and for the case of the presence of AF (curve 52). It may be recognized clearly that the maximum peak-to-peak amplitude of the averaged intraatrial impedance signal is comparatively very small in the case of an AF.

For long-term diagnostic purposes, the phases of the presence of an AF suspicion signal are stored in a memory MEM and may be transmitted wirelessly to a service center, for example, using a telemetry unit TEL.

In addition, the cardiac pacemaker has the typical components for rate-adaptive stimulation of the ventricle and the atrium, such as the stimulation units V-STIM and A-STIM, the sensing units V-SENS and A-SENS, the control unit CTRL and an activity sensor ACT, which allows the particular stimulation rate to be adapted to the physiological demand of a patient.

Moreover, the cardiac pacemaker may also be implemented as a cardioverter/defibrillator, particularly as an atrial defibrillator, and have atrial stimulation units adapted for this purpose, as are known in principle from the prior art.

What is claimed is:

1. A detector for atrial fibrillation and/or atrial flutter comprising:

an atrial input configured to receive an atrial signal representing an intraatrial electrogram or a time course of an intraatrial impedance;

a ventricular input configured to receive a ventricular event signal comprising information on an occurrence of a cyclically reoccurring ventricular event in chronological association to said atrial signal received via said atrial input;

an averaging unit that is configured to average a plurality of sections of said atrial signal, each section to be considered for averaging starts at a predefined offset with respect to a ventricular event and ends at the predefined offset before a next ventricular event, and wherein said averaging unit is further configured to put out an average atrial signal;

a peak amplitude determination unit that is configured to determine a peak-to-peak amplitude of said averaged atrial signal; and, a threshold comparator that is configured to compare said peak-to-peak amplitude of said averaged atrial signal to a predetermined reference value and to generate an AF warning signal if said peak-to-peak amplitude of said averaged atrial signal is less than said predetermined reference value.

2. The detector of claim 1 wherein said detector is configured to average a plurality of sequential sections.

3. The detector of claim 1 wherein said detector is configured to respond to an R-wave as said ventricular event.

4. The detector of claim 1 wherein said detector is configured to average a total number of eight current sections of said atrial signal.

5. The detector of claim 1 wherein said detector comprises an impedance measuring unit that comprises a measurement input that can be connected or that is connected to an atrial electrode lead for measurement of the intraatrial impedance and that is configured to generate an impedance signal that forms said atrial signal and that comprises a plurality of impedance values for each atrial cycle including an atrial contraction and an atrial relaxation immediately following said atrial contraction.

6. The detector of claim 5 wherein said impedance measuring unit is configured to sample said time course of said intraatrial impedance with a sampling rate between 30 Hz and 300 Hz.

7. The detector of claim 5 wherein said impedance measuring unit is configured to generate current pulses having an amperage between 100 μA and 600 μA and to deliver said current pulses via a neutral electrode and an intraatrial electrode and wherein said impedance measuring unit is further configured to measure a voltage drop between these electrodes when delivering a current pulse.

8. The detector of claim 7 wherein said impedance measuring unit is configured to generate current pulses each having a duration between 10 μs and 20 μs.

9. The detector of claim 8 wherein said impedance measuring unit is configured to generate pairs of current pulses each current pulse of such pair of current pulses having a same magnitude and duration but alternating polarity.

10. The detector of claim 9 wherein said impedance measuring unit is configured to generate pairs of current pulses wherein a sequence of polarity alternates from pair to pair.

11. The detector of claim 1 wherein said atrial input is connected to an atrial sensing stage and configured to pick up said intraatrial electrogram.

12. The detector of claim 11 wherein said atrial sensing stage or said detector is configured to sample said time course of said intraatrial electrogram with a sampling rate between 30 Hz and 300 Hz.

13. The detector of claim 1 wherein said detector further comprises a Wenckebach discriminator that is configured to respond to said AF warning signal and to discriminate AF from an AV block of second order, type Wenckebach and to clear said AF warning signal in case the AV block of second order, type Wenckebach is detected.

14. The detector of claim 13 wherein said Wenckebach discriminator is configured to determine an averaged duration of a ventricular cycle or RR-interval based on said ventricular event signal for a predetermined number of ventricular cycles and in case of an AF warning signal to compare a duration of a latest ventricular cycle with an averaged duration of said predetermined number of ventricular cycles and to determine whether only a single ventricular cycle or a plurality of consecutive ventricular cycles diverged from said averaged duration of said predetermined number of ventricular cycles by more than a predetermined threshold and to clear said AF warning signal in case that only a single ventricular cycle differs from said averaged duration of said predetermined number of ventricular cycles by more than said predetermined threshold.

15. The detector according to claim 13 wherein said Wenckebach discriminator is further configured to generate said predetermined threshold value by multiplying an averaged ventricular cycle duration of a predetermined number of recent ventricular cycles by a predetermined constant factor.

16. The detector according to claim 13 wherein said Wenckebach discriminator is further configured to generate a Wenckebach signal for each ventricular cycle that is a singular ventricular cycle that has a duration that diverges from an averaged duration of ventricular cycles by more than said predetermined threshold value.

17. The detector according to claim 16 wherein said Wenckebach discriminator comprises a counter that is configured to be incremented by one, if said Wenckebach discriminator has generated said Wenckebach signal.

18. The detector according to claim 17 wherein said counter is configured to be decremented by one, if said Wenckebach discriminator detects that two recent, consecutive ventricular cycles diverge from the averaged duration of ventricular cycles by more than said predetermined threshold.

19. The detector according to claim 17 wherein said counter is configured to be decremented by one, if said Wenckebach discriminator has not generated a Wenckebach signal for a plurality of at least five consecutive recent ventricular cycles.

20. The detector according to claim 18 wherein said detector is configured to clear said AF warning signal and to reset said counter if a counter value exceeds a predetermined counter value threshold.

21. The detector of claim 1 wherein said detector comprises an implantable medical device.

22. The detector of claim 21 wherein said implantable medical device is an implantable cardioverter/defibrillator.

23. A method for detecting atrial flutter and/or atrial fibrillation, said method comprising:
   acquiring an atrial signal over a time period that includes multiple ventricular heart cycles;
   acquiring a ventricular signal in chronological association with said atrial signal;
   determining a plurality of sequential sections of said atrial signal wherein each section begins at a predefined offset with respect to a ventricular event derived from said ventricular signal and ends at the predefined offset before a next ventricular event derived from said ventricular signal;
   averaging said plurality of sequential sections of said atrial signal thus forming an averaged atrial signal;
   determining a peak-to-peak amplitude of said averaged atrial signal;
   comparing said peak-to-peak amplitude to a predetermined reference value; and,
   generating an AF warning signal if said peak-to-peak amplitude is less than said predetermined reference value.

* * * * *